(12) United States Patent
Meghani et al.

(10) Patent No.: US 9,750,720 B2
(45) Date of Patent: *Sep. 5, 2017

(54) γ-AMINOBUTYRIC ACID (GABA) ANALOGUES FOR THE TREATMENT OF PAIN AND OTHER DISORDERS

(71) Applicant: Novassay S.A., Epalinges (CH)

(72) Inventors: Premji Meghani, Loughbourough (GB); Franz Kricek, Biedermannsdorf (AT)

(73) Assignee: Novassay, S.A., Epalinges (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/359,120

(22) Filed: Nov. 22, 2016

(65) Prior Publication Data

US 2017/0071909 A1    Mar. 16, 2017

Related U.S. Application Data

(63) Continuation of application No. 15/106,139, filed as application No. PCT/EP2014/077937 on Dec. 16, 2014.

(60) Provisional application No. 61/917,623, filed on Dec. 18, 2013.

(51) Int. Cl.

| | |
|---|---|
| *A61K 31/41* | (2006.01) |
| *A61K 31/4245* | (2006.01) |
| *C07D 257/04* | (2006.01) |
| *C07D 271/07* | (2006.01) |
| *C07C 259/14* | (2006.01) |
| *C07C 205/50* | (2006.01) |
| *C07C 233/10* | (2006.01) |
| *C07C 255/31* | (2006.01) |

(52) U.S. Cl.
CPC .......... *A61K 31/41* (2013.01); *A61K 31/4245* (2013.01); *C07C 205/50* (2013.01); *C07C 233/10* (2013.01); *C07C 255/31* (2013.01); *C07C 259/14* (2013.01); *C07D 257/04* (2013.01); *C07D 271/07* (2013.01); *C07B 2200/07* (2013.01); *C07C 2602/20* (2017.05)

(58) Field of Classification Search
CPC .... C07D 271/07; C07D 257/04; C07C 255/31
USPC ....................................................... 514/520
See application file for complete search history.

(56) References Cited

U.S. PATENT DOCUMENTS

2012/0071685 A1    3/2012    Kitegawa et al.
2016/0318885 A1*  11/2016   Meghani .............. C07D 257/04

FOREIGN PATENT DOCUMENTS

EP    2 192 109 A1    6/2010

OTHER PUBLICATIONS

Catterall, William A. *Structure and Regulation of Voltage-Gated Ca2+ Channels* (2000) Annu. Rev. Cell Dev. Biol., 16: 521-555.
Felix, Ricardo, Gurnett, Christina A., De Waard, Michel, and Campbell, Kevin P. *Dissection of Functional Domains of the Voltage-Dependent Ca2+ Channel α2δ Subunit* (1997) J. Neuroscience 17(18): 6884-6891.
Klugbauer, N., Lacinova, L., Marais, E., Hobom, M., and Hofmann, F. *Molecular Diversity of the Calcium Channel α2δ Subunit* (1999) J. Neuroscience 19(2): 684-691.
Hobom, M., Dai, S., Marais, E., Lacinova, L., Hofmann, F., and Klugbauer, N. *Neuronal Distribution and Functional Characterization of the Calcium Channel α2δ Subunit* (2000) Eur. J. Neurosci. 12(4): 1217-1226.
Qin, N., Yagel, S., Momplaisir, M.-L., Codd, E.E., and D'Andrea, M.R., *Molecular Cloning and Characterization of the Human Voltage-Gated Calcium Channel α2δ-4 Subunit* (2002) Mol. Pharmacol. 62(3): 485-496.

(Continued)

*Primary Examiner* — Kristin Vajda
(74) *Attorney, Agent, or Firm* — Matthew Karer; Adam Warwick Bell

(57) ABSTRACT

A compound of Formula 1

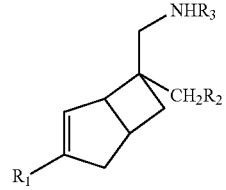

Formula 1 wherein $R_1$ represents hydrogen, halo, a C1-C4 alkyl group, a C1-C4 alkylhalide group, a C1-C4 alkoxy-C2-C4 alkyl group, a C2-C4 alkenyl group, a C2-C4 alkynyl group or a C3-C7 cycloalkyl group;

$R_2$ represents

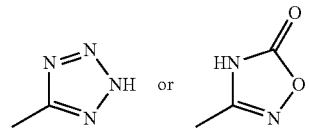

or a tautomer thereof; and $R_3$ represents hydrogen, a C1-C4 alkyl group, a C1-C4 alkoxy-C2-C4 alkyl group or a C3-C7 cycloalkyl group;

or a pharmaceutically acceptable salt or solvate thereof.

Processes to prepare said compounds and novel intermediates are also claimed. Such compound finds utility in treating neuropathic pain and disorders of the central nervous system.

17 Claims, No Drawings

(56) References Cited

OTHER PUBLICATIONS

Taylor, C.P., Gee, N.S., Su, T.-Z., Kocsis, J.D., Welty, D.F., Brown, J.P., Dooley, D.J., Boden, P., and Singh, L. *A summary of Mechanistic Hypotheses of Gabapentin Pharmacology* (1998) Epilepsy Res. 29: 233-249.
Dolphin, A.C. *The α2δ Subunits of Voltage-Gated Calcium Channels* (2013) Biochim. Biophys. Acta 1828: 1541-1549.
Su, T.Z.and Weber, M.L. *Mediation of Highly Concentrative Uptake of Pregabalin by L-Type Amino Acid Transport in Chinese Hamster Ovary and Caco-2 Cells* (2005) J. Pharmacol. Experimental Therapeutics 313(3): 1406-1415.
Fink, K., Dooley, D.J., Meder, W.P., Suman-Chauhan, N., Duffy, S., Clusmann, H., and Gothert, M. Inhibition of NeuronalCa2+ influx by Gabapentin and Pregabalin in the Human Neocortex (2002) Neuropharmacology 42: 229-236.
Piechan, J.L., Donevan, S., Taylor, C., Dickerson, M., and Li, Z. *PreGABAlin, a novel anticonvulsant, analgesic, and anxiolytic drug, exhibits class-specific α2δ-1 and α2δ-2 calcium channel subunit binding* (2004) Soc. Neuroscience Abstr., 111 (program No. 115) Online.
Calvo, D., Vazquez, M.J., Ashby, C., and Dominguez, J.M. *Kinetic Considerations on the Development of Binding Assay in Single-Addition Mode : Application to the Search for α2δ1 Modulators* (2012) J. Biomolecular Screening 17: 1041-1049.
Wang, M., Offord, J., Oxender, D.L., and Su, T.-Z. *Structural Requirement of the Calcium-Channel Subunit α2δfor Gabapentin Binding* (1999) Biochem. J. 342: 313-320.
Field, M.J., Cox, P.J., Stott, E., Melrose, H., Offord, J., Su, T.-Z., Bramwell, S., Corradini, L., England, S., Winks, J., Kinloch, R.A., Hendrich, J., Dolphin, A.C., and Williams D. *Identification of the α2δ1 Subunit of Voltage-Dependent Calcium Channels as a Molecular Target for pain Mediating the Analgesic Actions of Pregabalin* (2006) Proc. Natl. Acad. Sci. USA 103(46): 17537-17542.

\* cited by examiner

γ-AMINOBUTYRIC ACID (GABA) ANALOGUES FOR THE TREATMENT OF PAIN AND OTHER DISORDERS

The present invention relates to novel therapeutic agents, in particular to γ-aminobutyric acid derivatives, to pharmaceutical compositions thereof, to processes for their preparation, and to their therapeutic activity in the treatment of pain.

INTRODUCTION

Voltage-gated calcium channels are formed by combinations of the pore-forming a subunit and auxiliary proteins $\alpha_2\delta$, β, and γ (Caterall (2000) Annu. Rev. Cell Dev. Biol. 16:521-555). The $\alpha_2\delta$ protein is known to regulate both calcium channel density and the voltage-dependent kinetics of these channels (Felix et al (1997) J. Neuroscience 17: 6884-6891; Klugbauer et al (1999) J. Neuroscience 19:684-691; Hobom et al (2000) Eur. J. Neuroscience 12:1217-1226; and Qin et al (2002) Mol. Pharmacol. 62:485-496).

Gabapentin (GBP) is an anti-epileptic, anti-hyperalgesic and anxiolytic drug which binds with high affinity to two sub-types of calcium channel $\alpha_2\delta$ subunits $\alpha_2\delta_1$ and $\alpha_2\delta_2$. GBP was originally developed for epilepsy and has also found application in the treatment of pain and anxiety (Taylor et al (1998) Epilepsy Res. 29:223-249). The mechanism underlying GBP's action is still poorly understood. GBP was originally designed as a lipophilic γ-amino butyric acid (GABA) analogue, but has subsequently been shown not to interact with any of the enzymes on the GABA metabolic pathway, nor does it interact directly with the $GABA_A$ or $GABA_B$ receptors. However, it is able to efficiently cross the blood brain barrier via an L-system amino acid transporter.

Pregabalin (PGB) is a second generation, more potent, successor to GBP for the treatment of the same conditions as those listed above. GBP (Structure G, below) and PGB (Structure P, below) bind to the $\alpha_2\delta$-1 sub-unit with $IC_{50}$ values of 140 and 80 nM, respectively (Dolphin (2013) Biochim Biophys Acta 1828: 1541-1549).

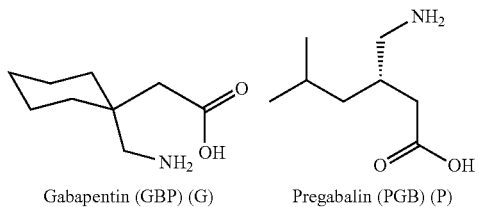

Gabapentin (GBP) (G)    Pregabalin (PGB) (P)

GBP shows few, if any, toxic side effects at clinically-relevant doses. It does, however, possess a relatively short half-life, being excreted unchanged, possibly due to very high water solubility and apparent lack of protein binding in vivo. Mild sedation, dizziness and ataxia are the main dose-limiting side effects and these are believed to be centrally-mediated.

GBP and PGB, unlike many other centrally-acting drugs, are hydrophilic and doubly-charged at neutral pH, making them insoluble in lipids, such as cell membranes. However, both compounds appear to cross membrane barriers of the gut, blood-brain barrier and cell membranes via a specialised transporter system (system L) that also transports endogenous amino acids, such as L-leucine, L-isoleucine and L-valine (Su et al (2005) J. Pharmacol. Exp. Ther. 313, 1-10).

In mammals, there are four related sub-types of the $\alpha_2\delta$ protein, each coded by a different gene. Each protein sub-type has a molecular weight of approximately 150 kD and consists of 997-1150 amino acid residues. Only $\alpha_2\delta$ sub-types 1 and 2 bind PGB with high affinity; sub-types 3 and 4 are devoid of significant drug binding (Fink et al (2002) Neuropharmacology, 42, 229-236). The binding affinity of PGB is similar for recombinant $\alpha_2\delta$ type 1 and type 2 proteins, demonstrating that PGB is not sub-type selective (Piechan et al (2004) Soc. Neuroscience Abstr., 111 (program No 115)).

European patent application 2192109A relates to bicyclic γ-amino acid compounds of Formula A

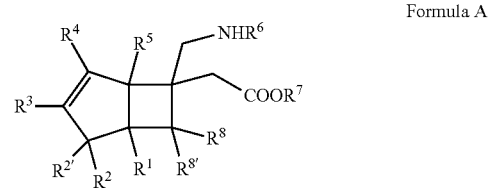

Formula A wherein $R_1$, $R_2$ $R_{2'}$ and R4-$R_8$ and $R_{8'}$ are each independently a hydrogen atom, a halogen atom, or a C1-C6 alkyl group, or $R_2$ and $R_{2'}$ together with the carbon atom to which they are bound form a C3-C7 cycloalkyl group; and $R_3$ is a hydrogen atom, a halogen atom, a C1-C6 alkyl group, a C1-C6 alkyl halide group, a hydroxy-C1-C6 alkyl group, a sulfanyl-C1-C6 alkyl group, a C1-C6 alkoxy-C1-C6 alkyl group, a C2-C6 alkenyl group, a C2-C6 alkynyl group, a C1-C6 alkoxy group, a C1-C6 alkylsulfanyl group, a C1-C6 alkylsulfanyl-C1-C6 alkyl group, a C2-C7 acylthio-C1-C6 alkyl group, a C2-C7 acyloxy-C1-C6 alkyl group, or a C3-C7 cycloalkyl group.

Said derivatives are disclosed to have activity as $\alpha_2\delta$ ligands and as being effective in the treatment of pain or central nervous system disorders. US 2012071685 discloses preparative methods to produce certain of said bicyclic γ-amino acid derivatives.

SUMMARY OF THE INVENTION

In one aspect, the present invention provides compounds of Formula 1

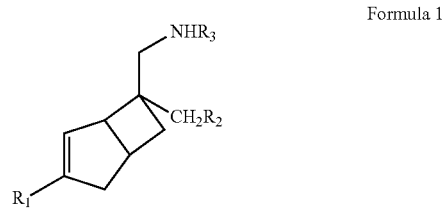

Formula 1 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_{2-4}$ alkynyl group or a $C_{3-7}$ cycloalkyl group;

$R_2$ represents

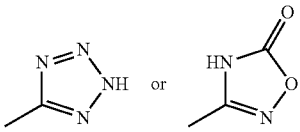

or a tautomer thereof; and $R_3$ represents hydrogen, a $C_{1-4}$ alkyl group, a ($C_{1-4}$ alkoxy)($C_{2-4}$ alkyl) group or a $C_{3-7}$ cycloalkyl group;

or a pharmaceutically acceptable salt or solvate thereof.

In another aspect, the present invention also provides a method of treating neuropathic pain in a subject, comprising the administration of a therapeutically effective amount of a compound of Formula 1 or a pharmaceutically acceptable salt or solvate thereof to said subject.

In a further aspect, the present invention provides a method of treating a disorder of the central nervous system in a subject, comprising the administration of a therapeutically effective amount of a compound of Formula 1 or a pharmaceutically acceptable salt or solvate thereof to said subject.

This invention provides compounds that bind with high affinity to the $\alpha_2\delta$-1 subunit of voltage-gated calcium channels.

In a yet further aspect, the present invention provides a pharmaceutical composition comprising the compounds disclosed herein together with a suitable excipient or a suitable lotion. The pharmaceutical composition may be in any convenient form for administration to a subject, for example, in the form of a capsule, a caplet, a tablet, or in the form of a topical ointment.

DETAILED DESCRIPTION OF THE INVENTION

The present invention relates to compounds of Formula 1

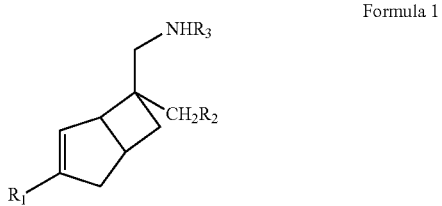

Formula 1 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_{2-4}$ alkynyl group or a $C_{3-7}$ cycloalkyl group;

$R_2$ represents

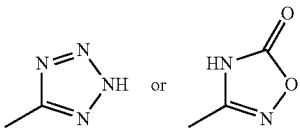

or a tautomer thereof; and $R_3$ represents hydrogen, a $C_{1-4}$ alkyl group, a ($C_{1-4}$ alkoxy)($C_{2-4}$ alkyl) group or a $C_{3-7}$ cycloalkyl group;

or a pharmaceutically acceptable salt or solvate thereof.

The following terms shall be understood to have the following meanings:

The term "$C_{1-4}$ alkyl" means a linear or branched aliphatic hydrocarbon chain having from 1 to 4 carbon atoms, for example methyl, ethyl, n-propyl, isopropyl, n-butyl, isobutyl or tert-butyl.

The term "$C_{1-4}$ alkylhalide" means a C1-4 alkyl group substituted with one or more halo atoms.

The term "($C_{1-4}$ alkoxy)($C_{2-4}$ alkyl)" means a $C_{2-4}$ alkyl group substituted with one or more $C_{1-4}$ alkoxy groups.

The term "C2-4 alkenyl" means a linear or branched aliphatic hydrocarbon chain having from 2 to 4 carbon atoms and containing a carbon-carbon double bond, for example ethenyl, propenyl, n-butenyl and isobutenyl.

The term "C2-4 alkynyl" means a linear or branched aliphatic hydrocarbon chain having from 2 to 4 carbon atoms and containing a carbon-carbon triple bond, for example ethynyl, propynyl, n-butynyl and isobutynyl.

The term "C3-7 cycloalkyl" means a non-aromatic mono- or multi-cyclic ring system of 3-7 carbon atoms, for example cyclopropyl, cyclobutyl, cyclopentyl, cyclohexyl and cycloheptyl.

The term "halo" means fluoro, chloro, bromo or iodo.

As used herein, the term "compounds of Formula 1" include pharmaceutically acceptable salts and solvates thereof. References to the intermediate compounds also include salts and solvates thereof. Pharmaceutically acceptable salts of the compounds of the invention may include basic addition salts of the compound. Such salts may be formed with an inorganic base which affords a pharmaceutically acceptable cation, for example, an alkali metal salt, such as a sodium or potassium salt, or an alkaline earth metal salt such as a calcium or magnesium salt. Pharmaceutically acceptable salts of the invention may also include acid addition salts. Such salts may be formed with an inorganic or organic acid which affords a pharmaceutically acceptable anion, for example a hydrohalide salt, such as a chloride or bromide salt, a sulphate or phosphate salt, or an organic acid salt, for example a salt with acetate, fumarate, maleate, tartrate, lactate, citrate, pyruvate, succinate, oxalate, methanesulphonate or p-toluenesulphonate. The term "solvate" refers to a compound of Formula 1 in the solid state, wherein molecules of a suitable solvent are incorporated in the crystal lattice. A suitable solvent for therapeutic administration is physiologically acceptable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Typical solvates include hydrates such as the monohydrate, dihydrate or trihydrate.

Where the compounds produced in accordance with the invention include a chiral centre, the compounds exist in two enantiomeric forms, accordingly the present compounds include the racemate, the single enantiomers or mixtures thereof. The enantiomers may be resolved by methods known to those skilled in the art, for example chiral high performance liquid chromatography (HPLC), for example silica with a bound chiral ligand. The enantiomers may also be resolved by methods involving formation of salts with chiral acids or bases to form diastereomeric salts followed by crystallisation. Compounds produced in accordance with the invention of the invention may also include single diastereoisomers or mixtures thereof. The diasteroeisomers may be separated by methods known to those skilled in the art, for example by formation of salts with acids or bases followed by crystallisation.

All tautomeric forms are also encompassed herein.

The term "therapeutically effective amount" describes the amount of a compound according to the present invention which needs to be used by human subjects in order to achieve a desired therapeutic effect. This amount may vary per subject and is dependent on parameters such as age, weight, height, physical condition and medical history. The compound according to the present invention may be effective to reduce, inhibit or ameliorate undesired symptoms in a patient.

In one embodiment of compounds according to the present invention, $R_1$ represents hydrogen, a $C_{1-4}$ alkyl group or halo, preferably hydrogen or a $C_{1-4}$ alkyl group, more preferably a $C_{1-4}$ alkyl group, for example methyl, ethyl or propyl. In further preferred compounds of Formula 1, $R_1$ represents ethyl.

In one embodiment of compounds according to the present invention, $R_3$ represents hydrogen or a C1-C4 alkyl group, for example methyl, ethyl or propyl. In preferred compounds of Formula 1, $R_3$ represents hydrogen or ethyl. In further preferred compounds of Formula 1, $R_3$ represents hydrogen.

In one embodiment, the invention is a compound of Formula 2:

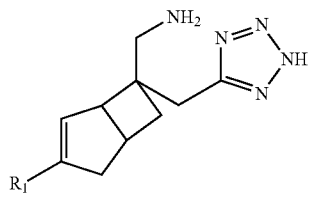

Formula 2 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_{2-4}$ alkynyl group or a $C_{3-7}$ cycloalkyl group;

or a pharmaceutically acceptable salt or solvate thereof.

The compound of Formula 2 may have specific stereochemistry as shown in a compound of Formula 2a

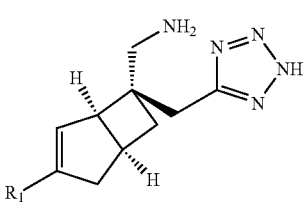

Formula 2a

In another embodiment, the invention is a compound of Formula 3:

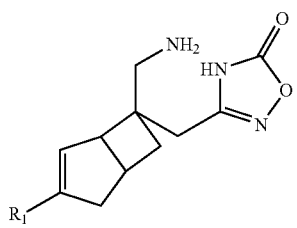

Formula 3 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_2$ alkynyl group or a $C_{3-7}$ cycloalkyl group;

or a pharmaceutically acceptable salt or solvate thereof.

The compound of Formula 3 may have specific stereochemistry as shown in a compound of Formula 3a

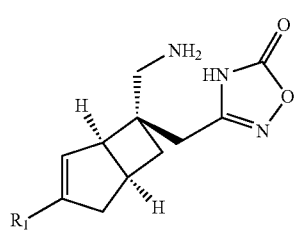

Formula 3a

In another embodiment, the invention is a compound of Formula 4:

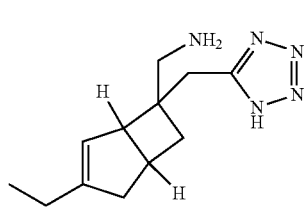

Formula 4

The compound of Formula 4 may have specific stereochemistry as shown in a compound of Formula 4a:

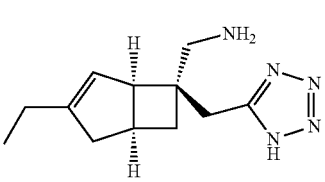

Formula 4a

In another embodiment, the invention is a compound of Formula 5:

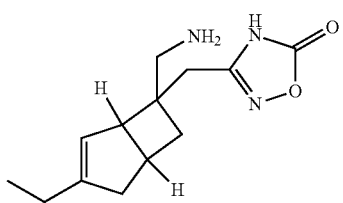

Formula 5

The compound of Formula 5 may have specific stereochemistry as shown in a compound of Formula 5a:

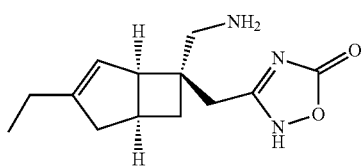

Formula 5a

Specific compounds of Formula 1 are:
3-(((1R,5S,6S)-6-(aminomethyl)-3-ethylbicyclo[3.2.0]hept-3-en-6-yl)methyl)-1,2,4-oxadiazol-5 (4H)-one
3-(((1S,5R,6R)-6-(aminomethyl)-3-ethylbicyclo[3.2.0]hept-3-en-6-yl)methyl)-1,2,4-oxadiazol-5(4H)-one
Racemic 3-(((1R,5S,6S)-6-(aminomethyl)-3-ethylbicyclo[3.2.0]hept-3-en-6-yl)methyl)-1,2,4-oxadiazol-5(4H)-one
((1R,5S,6S)-6-((1H-tetrazol-5-yl)methyl)-3-ethylbicyclo[3.2.0]hept-3-en-6-yl)methanamine
((1S,5R,6R)-6-((1H-tetrazol-5-yl)methyl)-3-ethylbicyclo[3.2.0]hept-3-en-6-yl)methanamine
Racemic ((1R,5S,6S)-6-((1H-tetrazol-5-yl)methyl)-3-ethylbicyclo[3.2.0]hept-3-en-6-yl)methanamine
N-(((1R,5S,6S)-6-((1H-tetrazol-5-yl)methyl)-3-ethylbicyclo[3.2.0]hept-3-en-6-yl)methyl)ethanamine
N-(((1S,5R,6R)-6-((1H-tetrazol-5-yl)methyl)-3-ethylbicyclo[3.2.0]hept-3-en-6-yl)methyl)ethanamine
Racemic N-(((1R,5S,6S)-6-((1H-tetrazol-5-yl)methyl)-3-ethylbicyclo[3.2.0]hept-3-en-6-yl)methyl)ethanamine The skilled person will understand that chiral molecules can be rotated but maintain the same relative stereochemical arrangement. For example, compounds of Formulae 4a and 5a may be depicted as below.

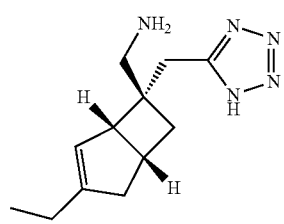

Formula 4a'

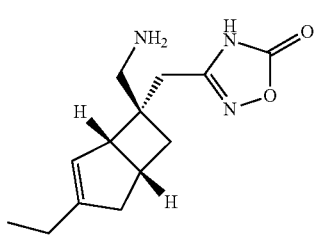

Formula 5a'

The present invention also provides pharmaceutical compositions comprising a therapeutically effective amount of a compound of Formula 1 together with a pharmaceutically acceptable carrier. The compound of Formula 1 is used in an amount effective to treat, reduce or ameliorate neuropathic pain in a subject, especially a human subject suffering from a painful condition. Such treatment of pain may or may not be associated with a central nervous system (CNS) or peripheral nervous system (PNS) disorder. The compound of Formula 1 is also effective to treat, reduce or ameliorate any other non-pain related CNS disorders. The compositions of the present invention comprise a therapeutically effective amount of the compound of Formula 1, which is generally in the range 0.1-95% w/w of the compound of Formula 1, but is dependent on the precise nature of the active and the mode of administration. Typically, the dose of active is in the range 0.1 to 500 mg as single or divided doses, depending on the precise nature of the active and the mode of administration.

In therapeutic use, the compounds of Formula 1 may be administered orally, rectally, parenterally or topically. The pharmaceutical compositions according to the present invention may take the form of any oral, rectal, parenteral or topical composition known to those skilled in the art, using carriers well known in the art of pharmacy. Such compositions are generally prepared in unit dosage form. Compositions for oral administration may include solid dosage forms, such as tablets, capsules or caplets, or liquid dosage forms, such as syrups and aqueous or oily suspensions. Solid dosage forms such as tablets and caplets may be prepared by mixing a compound of Formula 1 with an inert diluent in the presence of disintegrating agents and other formulation aids such as lubricants. Capsules may be in the form of hard capsules, for example hard gelatin capsules, or soft capsules which are prepared by conventional processes in which the active is incorporated in a carrier and encapsulated. Optionally, such dosages may include an enteric coating prepared according to conventional procedures which may be used to modify the release rate, or an excipient which delays release to provide a delayed release or a sustained release composition. Liquid dosage forms may be prepared by dissolving the active in a suitable liquid carrier such as water or an oily excipient, optionally in the presence of one or more dissolution agents, surfactants and/or suspending aids. Compositions for rectal administration are known pharmaceutical forms for such administration, for examples suppositories with a waxy or polyethylene glycol base. Compositions for parenteral administration are also known pharmaceutical forms for such administration, for examples sterile solutions or suspensions in a suitable solvent system. Compositions for topical administration may include creams, lotions, ointments, gels or other such dosages which may be administered by applying the composition directly to the affected area or by incorporating the composition in a vehicle such as a transdermal patch or as a composition contained within a permeable membrane for application to a painful area. Conventional aqueous and non-aqueous carriers, such as mineral oils and waxes may be used alone or in combination to prepare creams, lotions or ointments. Gels may be prepared by mixing the compound of Formula 1 with a topical vehicle comprising a gelling agent, e.g., Carbomer in the presence of water. Optionally further formulation aids such as transdermal accelerators, thickening agents may also be incorporated.

In another embodiment, the compound of the invention may be used in combination with a suitable pharmaceutical excipient for the topical treatment of back pain. The combination of the compound and the pharmaceutical excipient may be in the form of a gel, the gel shaped and adapted for placement upon the skin of a subject in pain. In another embodiment, the combination of the compound and the pharmaceutical excipient may be incorporated within the fabric of a patch, the patch shaped and adapted for placement upon and/or adhesion to the skin of a subject in pain. In a more preferred embodiment the compound is released at a slow rate from the pharmaceutical excipient within fabric of the patch.

The compounds of Formula 1 are incorporated in pharmaceutical compositions according to the present invention which are useful in the conditions recited below.

The invention contemplates that the compounds of Formula 1 may be used in a clinical setting for the treatment of neuropathic pain. In another embodiment, the compounds may be used for the treatment of pain in the central nervous system (CNS). In another embodiment, the compounds of the invention may be used for the treatment of pain which is not associated with the CNS. In a further embodiment, the compounds of the invention may be used for the treatment of pain which is not associated with the PNS. In yet another embodiment, the compounds of the invention may be used for the treatment of a CNS disorder. In one embodiment, the CNS disorder is selected from the group consisting of epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia. In another embodiment the compounds of the invention may be used in the treatment of pain in the CNS, such as, but not limited to, headache and migraine.

In another embodiment the compounds of the invention may be used in combination with a suitable lotion in a pharmaceutical formulation for the topical treatment of back pain. In another embodiment, the compounds of the invention may be used for the topical treatment of joint pain.

Processes for the preparation of compounds of the invention will now be described. These processes form a further aspect of the present invention.

Compounds of Formula 1 may be prepared by reduction of compounds of Formula 12

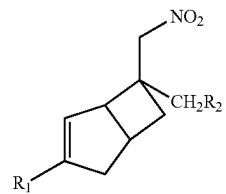

Formula 12 wherein $R_1$ and $R_2$ are as defined above, with a suitable reducing agent.

For example, compounds of Formula 1 in which $R_1$ is as herein defined,
$R_2$ represents

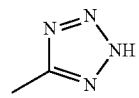

and $R_3$ represents a $C_{1-4}$ alkyl group, a $(C_{1-4}$ alkoxy$)(C_{2-4}$ alkyl) group or a $C_{3-7}$ cycloalkyl group, may be prepared by reduction of compounds of Formula 12 with a suitable reducing agent followed by a reductive amination with a suitable aldehyde or ketone. Suitable reagents include iron powder with ammonium chloride in a suitable solvent, for example an aqueous alcohol such as ethanol, at a suitable temperature, for example from ambient to refluxing temperatures. Further reductive amination in the presence of a suitable aldehyde or ketone with a suitable reducing agent, for example includes use of sodium borohydride in a suitable chlorinated or ethereal solvent such as dichloroethane at ambient temperature.

Compounds of Formula 1 in which $R_1$ is as herein defined,
$R_2$ represents

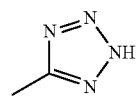

and $R_3$ represents hydrogen, may be prepared by reduction of compounds of Formula 12 with a suitable reducing agent, such as iron powder with ammonium chloride, in a solvent, such as aqueous ethanol, at a temperature, for example from ambient to refluxing temperatures. Addition of a protecting group to the crude product to produce intermediate compound of Formula 13

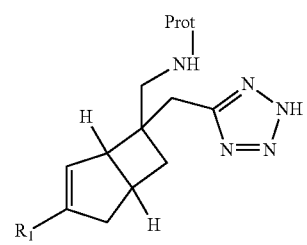

Formula 13 can be used to aid purification followed by deprotection under acidic conditions. Suitable protecting groups include a tert-butoxycarbonyl group obtained by reacting with di-tert-butyl dicarbonate in the presence of a suitable base and solvent. Examples of a suitable base include N,N-diisopropylethylamine or triethylamine in a suitable solvent such as an aqueous ethereal solvent, for example aqueous tetrahydrofuran, at ambient to refluxing temperatures. Deprotection can be effected with strong acids such hydrochloric acid or trifluoroacetic acid in a suitable solvent, for example trifluoroacetic acid in dichloromethane.

Compounds of Formula 1 in which $R_1$ and $R_3$ are as herein defined and $R_2$ represents

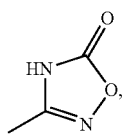

may be prepared by reacting compounds of Formula 12 with a suitable reducing agent, for example sodium borohydride in the presence of nickel (II) chloride hexahydrate in a suitable solvent, for example methanol, at 0° C. to ambient temperature.

Compounds of Formula 1 in which $R_3$ represents alkyl or cycloalkyl, may be generally prepared by reductive amination of compounds of Formula 1 in which $R_3$ represents hydrogen, for example by treatment with a suitable aldehyde or ketone compound together with a suitable reducing agent, such as sodium borohydride, sodium cyanoborohydride or sodium triacetoxyborohydride. For example, use of acetaldehyde produces compounds wherein $R_3$ is an ethyl group. Alternatively use of cyclopentanone produces compounds wherein $R_3$ is a cyclopentyl group.

Compounds of Formula 1 may also be generally prepared by removing a protecting group from compounds of Formula 1 where $R_3$ is replaced by a protecting group, for example $COOC(CH_3)_3$, which may be removed by reaction with a suitable acid, for example hydrochloric acid or trifluoroacetic acid.

Enantiomers of compounds of Formula 1 may be prepared by resolving the corresponding racemate or a mixture of diastereoisomers, for example by formation of diastereomeric salts with suitable chiral acids or bases. Examples of suitable chiral acids include: mandelic acid, α-methoxyphenylacetic acid, tartaric acid, naproxen or Mosher's acid. Examples of suitable chiral bases include: α-methylbenzylamine, 4-chloro-α-methylbenzylamine or ephedrine.

Compounds of Formula 12 in which $R_1$ is as herein defined and $R_2$ represents

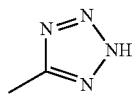

may be prepared from compounds of Formula 6

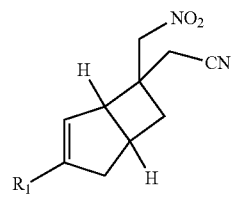

Formula 6 wherein $R_1$ is as herein defined, by a ring forming reaction with a suitable azide, for example, sodium- or trimethylsilyl-azide together with commonly known suitable catalysts such a dibutyltin oxide, pyridine hydrochloride or ammonium chloride in a solvent such as dimethylformamide (DMF), N-methylpyrrolidinone (NPO) or toluene, at elevated temperatures ranging from 60° C. to 120° C.

Compounds of Formula 12 in which $R_2$ represents

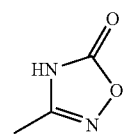

may be prepared by reacting a compound of Formula 6 with suitable reagents to produce the oxadiazolone moiety in a two-step procedure. For example, the first step may include use of hydroxylamine to produce the intermediate of Formula 9

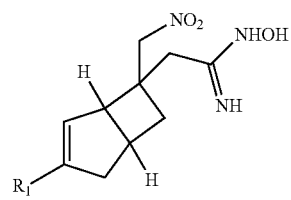

Formula 9 wherein $R_1$ is as herein defined. The second ring forming step may involve reacting intermediate 9 with a suitable cyclising reagent that incorporates a carbonyl group. For example, suitable reagents include carbonyldimidazole or phosgene. Treatment with carbonyl diimidazole may occur in a suitable ethereal solvent such as 1,4-dioxane at refluxing temperatures.

Compounds of Formula 9 may be prepared by treating compounds of Formula 6 with hydroxylamine in a suitable solvent such as aqueous ethanol at elevated temperatures, for example, in a microwave oven at 100 watts.

Compounds of Formula 6 may be prepared by treating compounds of Formula 7

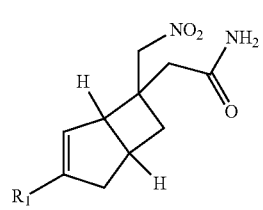

Formula 7 wherein R₁ is as herein defined, with a suitable dehydrating agent, for example a Burgess reagent in a suitable solvent, such as dichloromethane, at ambient temperature.

Compounds of Formula 7 may be prepared by treating compounds of Formula 8

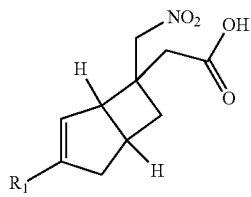

Formula 8 wherein R₁ is as herein defined, with a suitable coupling agent followed by addition of concentrated 0.88 aqueous ammonia. A suitable coupling agent may be 1-[bis(dimethylamino)methylene]-1H-1,2,3-triazolo[4,5-b]pyridinium 3-oxidhexafluorophosphate (HATU) in the presence of a suitable base, for example N,N-diisopropylethylamine (Hunig's base) or triethylamine, and a solvent such as dimethylformamide (DMF) or N-methylpyrrolidinone (NMP).

Compounds of Formula 8 may be prepared by treating a tert-butyl 2-(3-alkyl-6-(nitromethyl)bicyclo[3.2.0]hept-3-en-6-yl)acetate compound with a suitable strong acid, for example hydrochloric acid or trifluoroacetic acid, in a suitable solvent such as dichloromethane or 1,4-dioxane.

Tert-butyl 2-(3-alkyl-6-(nitromethyl)bicyclo[3.2.0]hept-3-en-6-yl)acetate compounds may be prepared as described in US 2012/0071685.

Compounds of Formula 6 may also be prepared by reacting compounds of Formula 14

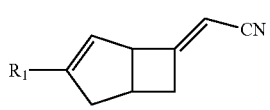

Formula 14 wherein R₁ is as herein defined, with nitromethane in the presence of a suitable base, for example 1,8-diazabicyclo[5.4.0]undec-7-ene (DBU), and a solvent such as dichloromethane.

Compounds of Formula 14 may be prepared by treating compounds of Formula 15

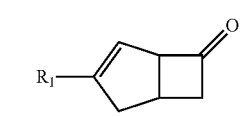

Formula 15 wherein R₁ is as herein defined, with a suitable double bond-forming reagent, for example diethyl cyanomethylphosphate, in the presence of a suitable base such as potassium tert-butoxide in a suitable solvent, for example tetrahydrofuran, at a temperature in the range 0° C. to ambient temperature.

Nitromethyl intermediate compounds 6, 7, 8, 9, 10, 11 and 12 may be encompassed by intermediate Formula 16

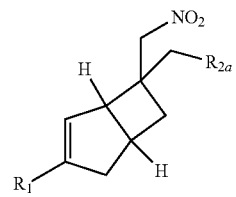

Formula 16 wherein R₁ represents hydrogen, halo, a $C_{1-4}$ alkyl group, a $C_{1-4}$ alkylhalide group, a $(C_{1-4}$ alkoxy)($C_{2-4}$ alkyl) group, a $C_{2-4}$ alkenyl group, a $C_{2-4}$ alkynyl group or a $C_{3-7}$ cycloalkyl group;

$R_{2a}$ represents —$R_2$, —CN, —CONH₂, —COOH, —(C=NH)NHOH; and

R₂ represents

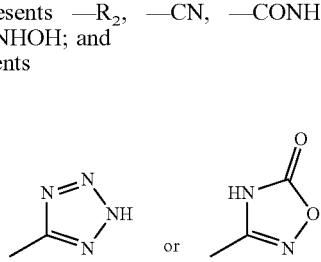

or a tautomer thereof.

Details of preferred process steps to prepare specific compounds of Formula 1 are set out in schemes 1-3 as follows:

Synthesis of the compound of Formula 4a is accomplished using the nitro-nitrile intermediate of Formula 6: (Scheme 1)

Scheme 1

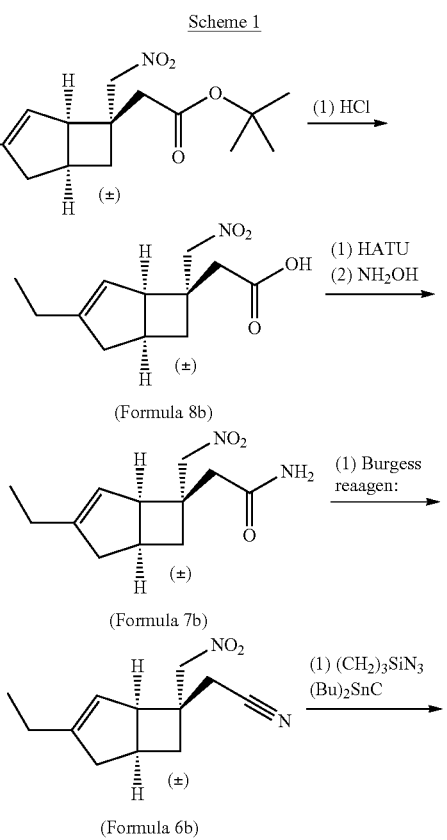

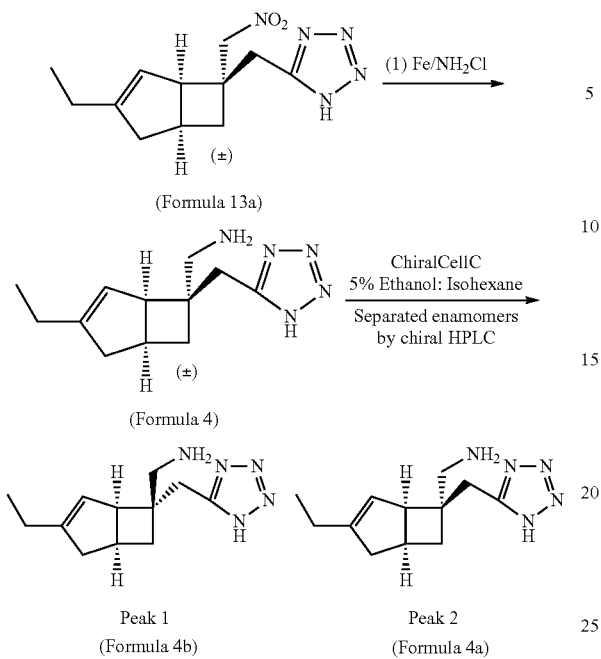

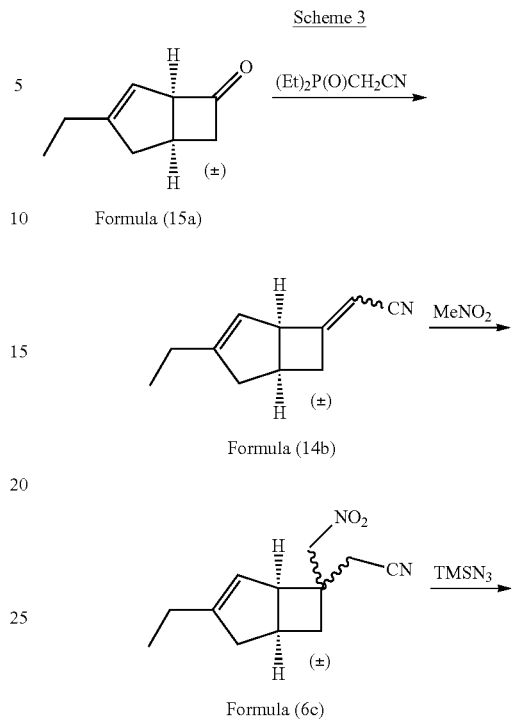

Synthesis of the compound of Formula 5 is accomplished using nitro-nitrile intermediate of Formula 6: (Scheme 2)

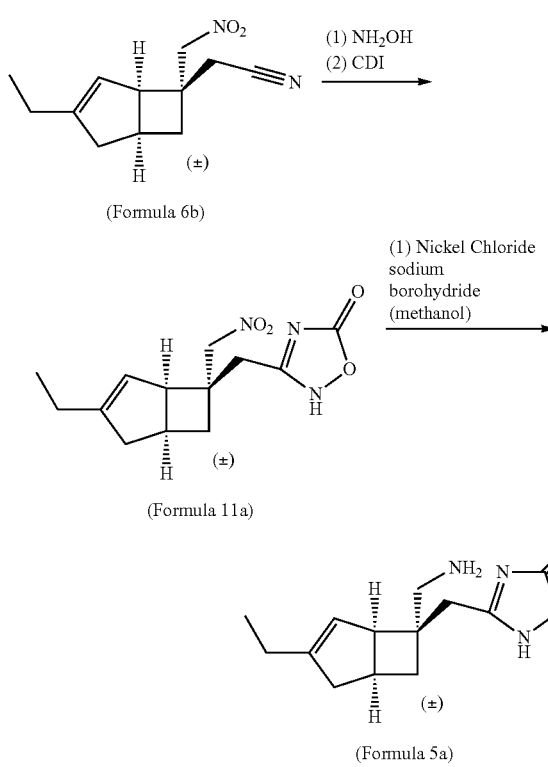

Synthesis of a compound of Formula 4 (shown as 4b) and its enantiomers may also be carried out by Scheme 3

Certain intermediate compounds and stereoisomers thereof of formulae 6, 7, 8, 9, 10, 11, 12, 13, 14 and 16 are believed to be novel compounds. The invention also contemplates all stereoisomers of intermediates of compounds comprising the chemical structure as shown in Formula 6, Formula 7, Formula 8, Formula 9, Formula 12, Formula 13, Formula 14 and Formula 16 and the specific compounds identified below.

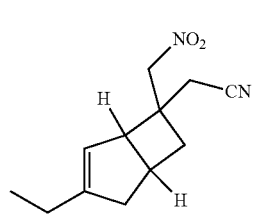

17
-continued (Formula 7a)
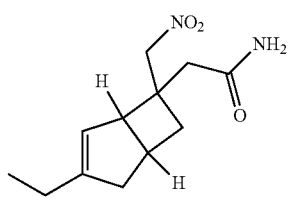

(Formula 8a)
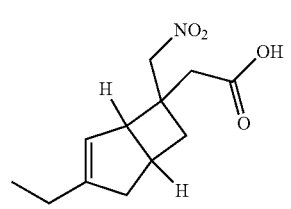

(Formula 9a)
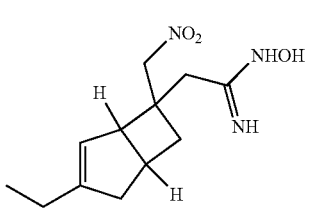

(Formula 10)
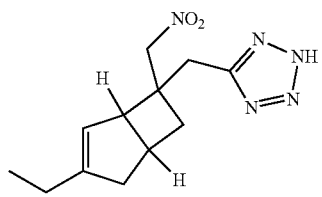

(Formula 11)
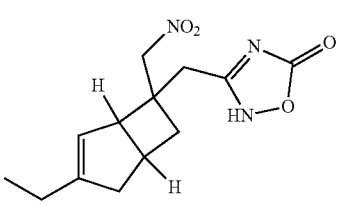

(Formula 13a)
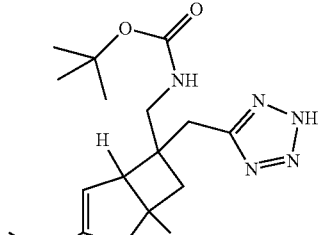

(Formula 14a)
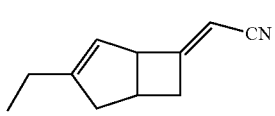

All novel compounds are claimed as a further aspect of the present invention.

18

The invention is illustrated by the following non-limitative Examples.

Example 1

Synthesis of Compound of Formula 3

Synthesis of racemic 3-(((1R,5S,6S)-6-(aminomethyl)-3-ethylbicyclo[3.2.0]hept-3-en-6-yl)methyl)-1,2,4-oxadiazol-5(4H)-one

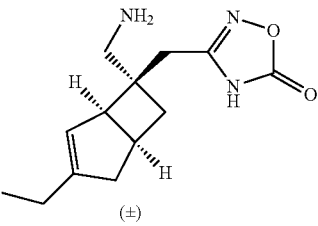 [SMILES: CCC1=C[C@@H]2[C@H](C1)C[C@]2(CN)Cc1noc(=O)[nH]1]

Step 1 (Compound of Formula 8)

Racemic 2-((1R,5S,6S)-3-ethyl-6-(nitromethyl)bicyclo[3.2.0]hept-3-en-6-yl)acetic acid

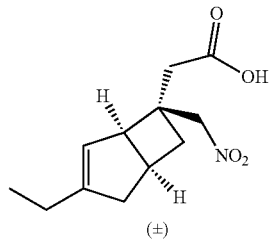 [SMILES: CCC1=C[C@@H]2[C@H](C1)C[C@]2(CC(=O)O)C[N+](=O)[O-]]

To a solution of tert-butyl 2-(3-ethyl-6-(nitromethyl)bicyclo[3.2.0]hept-3-en-6-yl)acetate (1.8 g, 6.09 mmol) [preparation described in patent US2012/0071685A1, Example 5-d] in dichloromethane (20 ml) was added trifluoroacetic acid (20 ml) and the mixture allowed to stand for 1 hour. The solvent was removed and the residue redissolved in toluene (100 ml) and evaporated to dryness, this procedure was repeated ×5 to give 2-(3-ethyl-6-(nitromethyl)bicyclo[3.2.0]hept-3-en-6-yl)acetic acid (1.4 g, 5.62 mmol, 92% yield) as a colourless oil.

LCMS (Agilent, X-Select, Waters X-Select C18, 2.5 μm, 4.6×30 mm, Acidic (0.1% formic acid) 4 min method, 5-95% acetonitrile/water): m/z; 238(M−H)⁻ (ES⁻), at 2.21 min, 93% purity@215 nm.

$^1$H NMR (400 MHz, DMSO-d6): δ 12.25 (1H, s), 5.26 (1H, d, J=2.0), 4.87 (2H, d, J=1.6), 3.13 (1H, br. s), 2.85 (1H, quin, J=7.5), 2.46-2.32 (3H, m), 2.21 (1H, ddd, J=12.5, 8.8, 2.5), 2.11 (2H, q, J=7.4), 2.03 (1H, br. d, J=16.5), 1.46 (1H, dd, J=11.3, 7.3), 1.04 (3H, t, J=7.4) ppm. (Toluene also present: 7.26-7.23 (0.3H, m), 7.18-7.12 (0.45H, m), 2.30 (0.45H, m).

Step 2 (Compound of Formula 7)

Racemic 2-((1R,5S,6S)-3-ethyl-6-(nitromethyl)bicyclo[3.2.0]hept-3-en-6-yl)acetamide

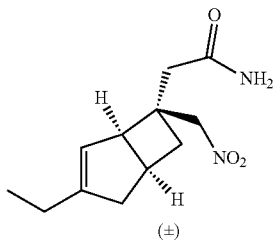 [SMILES: CCC1=C[C@@H]2[C@H](C1)C[C@]2(CC(N)=O)C[N+](=O)[O-]]

To a solution of 2-(3-ethyl-6-(nitromethyl)bicyclo[3.2.0]hept-3-en-6-yl)acetic acid (2.5 g, 10.45 mmol) in dry dimethylformamide (10 ml) was added Hunig's Base (2.74 ml, 15.67 mmol) followed by HATU (4.37 g, 11.49 mmol). The mixture was allowed to stir for 10 minutes at room temperature, and then cooled in ice water. To this cooled stirred solution was added 0.88 aqueous ammonia solution (6.46 ml, 104 mmol). The reaction mixture was then allowed to warm to room temperature and stirred for a further 1 hour. The solvent was removed by rotary evaporation and the residue taken up into ethyl acetate and washed with water, dried over sodium sulfate. The crude product was purified by silica chromatography (40 g silica column, solvent gradient 20-100% ether:isohexane) to afford 2-(3-ethyl-6-(nitromethyl)bicyclo[3.2.0]hept-3-en-6-yl)acetamide (2.3 g, 9.46 mmol, 91% yield) as a clear colourless gum.

LCMS (Agilent, X-Select, Waters X-Select C18, 2.5 µm, 4.6×30 mm, Acidic (0.1% formic acid) 4 min method, 5-95% acetonitrile/water): m/z 239(M+H)+(ES+); 237(M−H)−(ES−), at 1.949 min.

$^1$H NMR (400 MHz, DMSO-d6): δ 7.28 (1H, br. s), 6.77 (1H, br. s), 5.27 (1H, d, J=2.2), 4.88 (2H, dd, J=22.3, 12.3), 3.12 (1H, br. s), 2.85 - 2.78 (1H, m), 2.46 - 2.39 (1H, m), 2.24 (1H, br. d, J=1.4), 2.19 (1H, ddd, J=12.4, 8.8, 2.6), 2.11 (2H, q, J=7.5), 2.00 (1H, br. d, J=16.8), 1.42 (1H, dd, J=12.5, 7.4), 1.05 (3H, t, J=7.4) ppm. (DCM also present: 5.87 (0.9 H, s))

Step 3 (Compound of Formula 6)

Racemic 2-((1R,5S,6S)-3-ethyl-6-(nitromethyl)bicyclo[3.2.0]hept-3-en-6-yl)acetonitrile

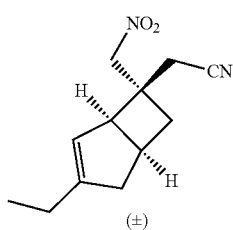 [SMILES: CCC1=C[C@@H]2[C@H](C1)C[C@@]2(CC#N)C[N+](=O)[O-]]

To an ice-cooled solution of racemic 2-((1R,5S,6S)-3-ethyl-6-(nitromethyl)bicyclo[3.2.0]hept-3-en-6-yl)acetamide (0.8 g, 3.36 mmol) in dry dichloromethane (20 ml) was added portionwise over 20 mins Burgess reagent (0.880 g, 3.69 mmol) and the mixture allowed to warm to room temperature and stirred for 3 hours. The reaction mixture was evaporated to half volume and applied to a silica cartridge and purified by chromatography on the Companion (40 g column, 0-60% ether:isohexane) to afford racemic 2-((1R,5S,6S)-3-ethyl-6-(nitromethyl)bicyclo[3.2.0]hept-3-en-6-yl)acetonitrile (501 mg, 2.23 mmol, 66.4% yield) as a clear colourless oil.

LCMS (Agilent, X-Select, Waters X-Select C18, 2.5 µm, 4.6×30 mm, Acidic (0.1% formic acid) 4 min method, 5-95% acetonitrile/water): m/z 221(M+H)+(ES+); 219(M−H)−(ES−), at 2.34.

$^1$H NMR (400 MHz, DMSO-d6): δ 5.33 (1H, d, J=2.0), 4.87 (2H, d, J=1.9), 3.17 (1H, br. s), 2.93-2.85 (1H, m), 2.65 (2H, br. s), 2.49-2.43 (1H, m), 2.23 (1H, ddd, J=12.5, 8.8, 2.5), 2.16-2.05 (3H, m), 1.56 (1H, dd, J=12.6, 7.2), 1.07 (3H, t, J=7.4) ppm.

Step 4 (Compound of Formula 9)

Racemic 2-((1R,5S,6S)-3-ethyl-6-(nitromethyl)bicyclo[3.2.0]hept-3-en-6-yl)-N-hydroxyacetimidamide

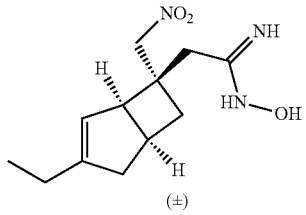 [SMILES: CCC1=C[C@@H]2[C@H](C1)C[C@@]2(CC(=N)NO)C[N+](=O)[O-]]

A mixture of hydroxylamine in water (50% aqueous solution) (543 8µl, 8.85 mmol), racemic 2-((1R,5S,6S)-3-ethyl-6-(nitromethyl)bicyclo[3.2.0]hept-3-en-6-yl)acetonitrile (650 mg, 2.95 mmol) in ethanol (10 ml) was heated at 85 degrees C. in a CEM microwave at 100 Watts for 2 hours.

The reaction mixture was evaporated to dryness and the residue taken up into ethyl acetate and washed with water and dried over sodium sulfate. Filtration and evaporation gave racemic 2-((1R,5S,6S)-3-ethyl-6-(nitromethyl)bicyclo[3.2.0]hept-3-en-6-yl)-N-hydroxyacetimidamide (530 mg, 1.883 mmol, 63.8% yield) as a colourless oil, which was used without further purification.

LCMS (Agilent, X-Select, Waters X-Select C18, 2.5 µm, 4.6×30 mm, Acidic (0.1% formic acid) 4 min method, 5-95% acetonitrile/water): m/z 254 (M+H)+(ES+); at 1.25 min.

$^1$H NMR (400 MHz, DMSO-d6): δ8.92 (1H, s), 5.36 -5.35 (1H, m), 5.26 (2H, br. s), 4.96 (1H, d, J=12.8), 4.83 (1H, d, J=12.8), 3.13 (1H, br. s), 2.77 (1H, quin, J=7.5), 2.41 (1H, dd, J=16.4, 8.2), 2.20-2.09 (5H, m), 2.02 (1H, d, J=16.0), 1.53 (1H, dd, J=12.4, 7.4), 1.06 (3H, t, J=7.4) ppm.

Step 5 (Compound of Formula 11)

Racemic 3-(((1R,5S,6S)-3-ethyl-6-(nitromethyl)bicyclo[3.2.0]hept-3-en-6-yl)methyl)-1,2,4-oxadiazol-5(4H)-one

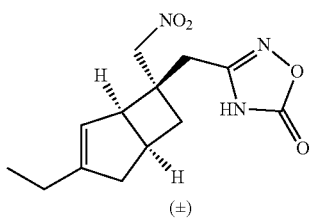 [SMILES: CCC1=C[C@@H]2[C@H](C1)C[C@@]2(Cc1noc(=O)[nH]1)C[N+](=O)[O-]]
(±)

A mixture of racemic 2-((1R,5S,6S)-3-ethyl-6-(nitromethyl)bicyclo[3.2.0]hept-3-en-6-yl)-N-hydroxyacetimidamide (520 mg, 2.053 mmol) and carbonyl diimidazole (666 mg, 4.11 mmol) in dioxane (30 mL) was heated under reflux for 2 hours.

The reaction mixture was evaporated to dryness and the residue taken up into water (50 ml) and the solution carefully acidified with 1N HCL. The aqueous mixture was extracted into ether and dried over sodium sulfate.

The crude product was purified by silica chromatography (12 g column, solvent: ether) to afford racemic 3-(((1R,5S,6S)-3-ethyl-6-(nitromethyl)bicyclo[3.2.0]hept-3-en-6-yl)methyl)-1,2,4-oxadiazol-5(4H)-one (195 mg, 0.684 mmol, 33.3% yield) as a colourless gum.

LCMS (Agilent, X-Select, Waters X-Select C18, 2.5 μm, 4.6×30 mm, Basic (0.1% Ammonium Bicarbonate) 4 min method, 5-95% acetonitrile/water): 278(M−H)⁻ (ES⁻), at 1.58 min, 98% purity@215 nm.

$^1$H NMR (400 MHz, DMSO-d6): δ 12.12 (1H, s), 5.35 (1H, q, J=1.9), 4.88 (2H, q, J=13.5), 3.16 (1H, br. s), 2.87 91H, quin, J=7.5), 2.66 (2H, d, J=1.4), 2.44 (1H, dd, J=16.6, 7.8), 2.17-2.09 (3H, m), 2.06-2.02 (1H, m), 1.62 (1H, dd, J=12.5, 7.4), 1.06 (3H, t, J=7.5). Ether present–overlaps with signal at 1.06+water signal at 3.4 ppm $^{13}$C NMR (100 MHz, DMSO-d6): δ 159.44, 157.15, 150.69, 120.63, 80.09, 52.17, 42.75, 41.80, 35.38, 30.19, 28.46, 23.87, 12.25 ppm Step 6 (Compound of Formula 3)

Racemic 3-(((1R,5S,6S)-6-(aminomethyl)-3-ethylbicyclo[3.2.0]hept-3-en-6-yl)methyl)-1,2,4-oxadiazol-5(4H)-one

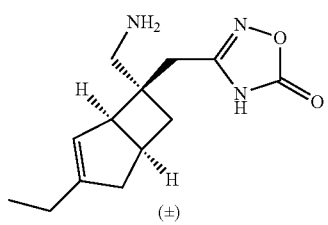 [SMILES: CCC1=C[C@@H]2[C@H](C1)C[C@]2(CN)Cc1noc(=O)[nH]1]
(±)

To an ice-cooled solution of racemic 3-(((1R,5S,6S)-3-ethyl-6-(nitromethyl)bicyclo[3.2.0]hept-3-en-6-yl)methyl)-1,2,4-oxadiazol-5(4H)-one (286 mg, 1.024 mmol), and nickel(II) chloride, 6H$_2$O (24.34 mg, 0.102 mmol) in methanol (40 ml) was added portionwise sodium borohydride (387 mg, 10.24 mmol) portion wise over 15 mins. Upon completion of addition, the reaction mixture was allowed to warm to room temp.

The reaction mixture was carefully quenched with the addition of acetic acid (1 ml) and the mixture evaporated to dryness. The residue was taken up into methanol and passed through a plug of silica and the eluant was evaporated to dryness to give an off white solid. The crude product was purified by preparative HPLC (Waters, Acidic (0.1% Formic acid), Acidic, Waters X-Select Prep-C18, 5 μm, 19×50 mm column, 25-70% acetonitrile in Water) to afford after lyophilisation racemic 3-(((1R,5S,6S)-6-(aminomethyl)-3-ethylbicyclo[3.2.0]hept-3-en-6-yl)methyl)-1,2,4-oxadiazol-5(4H)-one (8.0 mg, 0.031 mmol, 3.07% yield) as a colourless solid.

LCMS (Agilent, X-Select, Waters X-Select C18, 2.5 μm, 4.6×30 mm, Acidic (0.1% Formic acid) 4 min method, 5-95% acetonitrile/water): m/z 250(M+H)⁺ (ES⁺); 248(M−H)⁻ (ES⁻), at 1.143 min, 100% purity@215 nm.

$^1$H NMR (400 MHz, DMSO-d6): δ 8.27 (0.5H, s), 5.33 (1H, d, J=1.5), 3.11 (1H, d, J=13.1), 3.04 (1H, J=13.1), 2.97 (1H, br. s), 2.76 (1H, quin, J=7.5), 2.44-2.34 (3H, m), 2.12 (2H, q, J=7.4), 2.03-1.97 (2H, m), 1.31 (1H, dd, J=12.2, 7.4), 1.05 (3H, t, J=7.4) ppm.

$^{13}$C NMR (100 MHz, DMSO-d6): δ 170.67, 165.86, 149.09, 121.20, 51.92, 46.98, 42.62, 41.81, 34.69, 32.98, 30.35, 24.11, 12.64 ppm Example 2

Synthesis of Compound of Formula 2

Synthesis of racemic ((1R,5S,6S)-6-((1H-tetrazol-5-yl)methyl)-3-ethylbicyclo[3.2.0]hept-3-en-6-yl)methanamine and enantiomers

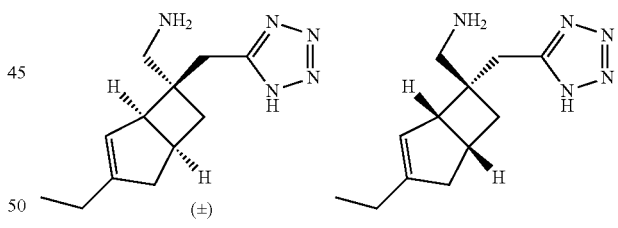
(±)                                    Peak 1

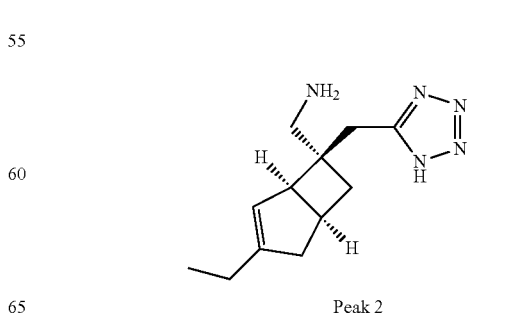
Peak 2

Step 1 (Compound of Formula 10)

Racemic 5-(((1R,5S,6S)-3-ethyl-6-(nitromethyl)bicyclo[3.2.0]hept-3-en-6-yl)methyl)-1H-tetrazole

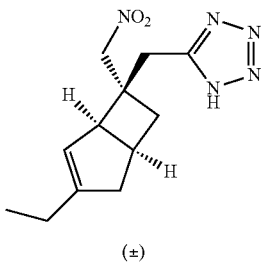 [SMILES: CCC1=C[C@@H]2[C@H](C1)C[C@@]2(Cc1nnn[nH]1)C[N+](=O)[O-]]

(±)

To a solution of racemic 2-((1R,5S,6S)-3-ethyl-6-(nitromethyl)bicyclo[3.2.0]hept-3-en-6-yl)acetonitrile (280 mg, 1.271 mmol) (preparation described in Step 3, of compound of Formula 3) in dry toluene (5 ml) was added azidotrimethylsilane (675 5.08 mmol) and dibutyltin oxide (63.3 mg, 0.254 mmol) and the mixture heated in a CEM microwave oven: Power 100 Watts, temperature 110 degrees for 1 hour.

The above process was repeated eleven times and the crude reaction mixtures combined. The combined reaction mixture was evaporated to dryness and the residue taken up into 0.1N sodium hydroxide solution (10 ml) and washed with ether (2×20 ml) the aqueous layer was separated and acidified with 1N hydrochloric acid. The crude product was then re-extracted back into ether and dried over sodium sulfate. Filtration and evaporation gave a solid which was purified by chromatography on the Companion (4 g column, solvent gradient: 10-70% ether:isohexane) to afford racemic 5-(((1R,5S,6S)-3-ethyl-6-(nitromethyl)bicyclo[3.2.0]hept-3-en-6-yl)methyl)-1H-tetrazole (1.81 g, 5.50 mmol, 39% yield) as a colourless solid.

LCMS (Agilent, X-Select, Waters X-Select C18, 2.5 μm, 4.6×30 mm, Acidic (0.1% formic acid) 4 min method, 5-95% acetonitrile/water): m/z 264(M+H)$^+$ (ES$^+$); 262(M−H)$^-$ (ES$^-$), at 2.05 min, 98% purity@210 nm. $^1$H NMR (400 MHz, DMSO-d6): δ 16.12 (1H, br. s), 5.37 (1 H, d, J=1.0), 4.80 (2H, s), 3.22 (1H, br. s), 3.02 (2H, s), 2.92-2.84 (1H, m), 2.50-2.44 (1H, m), 2.18-2.05 (4H, m), 1.64 (1H, dd, J=12.4, 7.4), 1.06 (3H, t, J=7.4) ppm.

Step 2 (Compound of Formula 13)

Racemic tert-butyl (((1R,5S,6S)-6-((1H-tetrazol-5-yl)methyl)-3-ethylbicyclo[3.2.0]hept-3-en-6-yl)methyl)carbamate

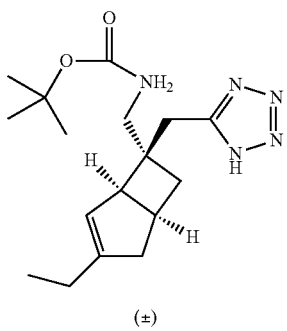 [SMILES: CCC1=C[C@@H]2[C@H](C1)C[C@]2(CNC(=O)OC(C)(C)C)Cc1nnn[nH]1]

(±)

To a solution of racemic 5-(((1R,5S,6S)-3-ethyl-6-(nitromethyl)bicyclo[3.2.0]hept-3-en-6-yl)methyl)-1H-tetrazole (400 mg, 1.519 mmol) in a solvent of ethanol (50 ml) and water (15 ml) was added iron powder (848 mg, 15.19 mmol) and ammonium chloride (488 mg, 9.12 mmol). The mixture was stirred and heated at reflux for 1 hour. The reaction mixture was allowed to cool and filtered through a pad of celite and washed well with ethanol and the filtrate evaporated to dryness.

The above residue was dissolved in a mixture of water (20 ml) and tetrahydrofuran (60 ml) was to this solution was added di-tert-butyl dicarbonate (2.8 g, 12.86 mmol) and triethylamine (1.79 ml, 12.86 mmol) and then heated and stirred at 40 deg for 1 hour. The reaction mixture was evaporated to half volume and the residue acidified by the addition of 10% aqueous citric acid solution. The crude product was then extracted into ethyl acetate, the organics separated, washed with water and dried over sodium sulfate. The crude product was purified by silica chromatography (12 g column, solvent gradient 0-70% ether:isohexane) to afford racemic tert-butyl (((1R,5S,6S)-6-((1H-tetrazol-5-yl)methyl)-3-ethylbicyclo[3.2.0]hept-3-en-6-yl)methyl)carbamate (380 mg, 1.140 mmol, 89% yield) as a clear colourless gum.

LCMS (Agilent, X-Select, Waters X-Select C18, 2.5 μm, 4.6×30 mm, Acidic (0.1% formic acid) 4 min method, 5-95% acetonitrile/water): m/z 334(M+H)$^+$ (ES$^+$); 332(M−H)$^-$ (ES$^-$), at 2.34 min, 98% purity@210 nm.

LCMS (Agilent, X-Select, Waters X-Bridge C18, 2.5 μm, 4.6×30 mm, Basic (0.1% Ammonium Bicarbonate) 4 min method, 5-95% acetonitrile/water): m/z 334(M+H)$^+$ (ES$^+$); 332(M−H)$^-$ (ES$^-$), at 1.51 min, 98% purity@215 nm.

$^1$H NMR (400 MHz, CD$_3$OD): δ 6.96 (1H, t, J=5.8), 5.43 (1H, br. s), 3.27-3.15 (2H, m), 3.11 (1H, br. s), 2.99 (1H, d, J=14.9), 2.89 (1H, d, J=14.9), 2.84-2.76 (1H, m), 2.51 (1H, dd, J=16.4, 7.8), 2.17 (2H, q, J=7.4), 2.07 (1H, br. d, J=16.4), 1.90 (1H, ddd, J=11.8, 8.7, 2.6), 1.56 (1H, dd, J=12.1, 7.3), 1.46 (7H, s, $^t$Bu(major rotamer)), 1.44 (2H, s, $^t$Bu(minor rotamer)), 1.11 (3H, t, J=7.5) ppm. (Dichloromethane also present: 5.49 (0.5H, s))

Step 3 (Compound of Formula 2)

Racemic ((1R,5S,6S)-6-((1H-tetrazol-5-yl)methyl)-3-ethylbicyclo[3.2.0]hept-3-en-6-yl)methanamine

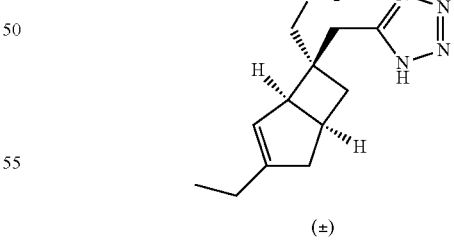

(±)

To a solution of racemic tert-butyl (((1R,5S,6S)-6-((1H-tetrazol-5-yl)methyl)-3-ethylbicyclo[3.2.0]hept-3-en-6-yl)methyl)carbamate (1.3 g, 3.90 mmol) in dichloromethane (50 ml) was added trifluoroacetic acid (30 ml, 389 mmol) and the mixture allowed to stand at room temperature for 30 minutes.

The mixture was evaporated to dryness and residue was redissolved in toluene (60 ml) and evaporated to dryness, this procedure was repeated three times. The residue was dissolved in a 1:1 mixture of methanol and water (30 m). This solution was applied to a DOWEX 50WX8 hydrogen form 100-200 mesh ion exchange resin (10 g). The resin was washed eluted with water until the eluant was neutral. The product was then eluted using 2N methanolic ammonia solution to give after evaporation a colourless gum. This residue was triturated with acetonitrile (13 ml) to give racemic ((1R,5S,6S)-6-((1H-tetrazol-5-yl)methyl)-3-ethylbicyclo[3.2.0]hept-3-en-6-yl)methanamine as a colourless solid (365 mg, 1.50 mmol, 38.5%).

LCMS (Agilent, X-Select, Waters X-Select C18, 2.5 µm, 4.6×30 mm, Acidic (0.1% formic acid) 4 min method, 5-95% acetonitrile/water): m/z 234(M+H)$^+$ (ES$^+$); 232(M−H)$^−$ (ES$^−$), at 1.01 min.

LCMS (Agilent, X-Select, Waters X-Bridge C18, 2.5 µm, 4.6×30 mm, Basic (0.1% Ammonium Bicarbonate) 4 min method, 5-95% acetonitrile/water): , m/z 234(M+H)$^+$ (ES$^−$); 232(M−H)$^−$ (ES$^−$), at 1.21 min.

$^1$H NMR (400 MHz, CD$_3$OD): δ 5.40 (1H, d, J=1.8), 3.15 (3H, m), 3.05 (1H, d, J=15.3), 2.94 (1H, d, J=15.3), 2.83 (1H, m), 2.52 (1H, br. dd, J=16.4, 7.8), 2.19 (2H, q, J=7.8), 2.10 (1H, br. d), 1.93 (1H, ddd, J=12.4, 8.7, 2.7), 1.64 (1H, dd, J=12.6, 7.5), 1.13 (3H, t, J=7.4) ppm.

$^{13}$C NMR (100 MHz, CD$_3$OD): δ 159.86, 151.60, 122.57, 53.69, 47.96, 44.73, 43.03, 36.87, 30.21, 25.40, 12.84 ppm Step 4

Chiral Resolution of Enantiomers of Racemic ((1R,5S,6S)-6-((1H-tetrazol-5-yl)methyl)-3-ethylbicyclo[3.2.0]hept-3-en-6-yl)methanamine

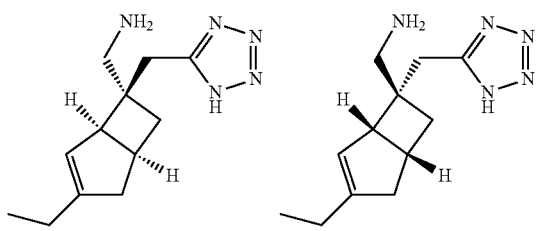 [SMILES: CCC1=C[C@@H]2[C@H](C1)C[C@]2(CN)Cc1nnn[nH]1 ; CCC1=C[C@H]2[C@@H](C1)C[C@@]2(CN)Cc1nnn[nH]1]

Racemic ((1R,5S,6S)-6-((1H-tetrazol-5-yl)methyl)-3-ethylbicyclo[3.2.0]hept-3-en-6-yl)methanamine (155 mg) was resolved using a Diacel Chiralpak IC, 5 µm, 20×250 mm, 15 ml/min, 50% ethanol:50% isohexane. To obtain after evaporation of the fractions peak 1 retention time 9.91 min (32 mg) and peak 2 retention time 18.91 min (28 mg).

Analytical Chiral chromatography: Diacel Chiralpak IC, 5 µm, 4.6×250 mm, 30 min method, 1.5 ml/min, 30% ethanol:70% isohexane peak 1 retention time 9.49 min %, peak 2 retention time 19.41 min at 215 nm.

Example 3

Synthesis of Compound of Formula 2

Synthesis of Racemic N-(((1R,5S,6S)-6-((1H-tetrazol-5-yl)methyl)-3-ethylbicyclo[3.2.0]hept-3-en-6-yl)methyl)ethanamine

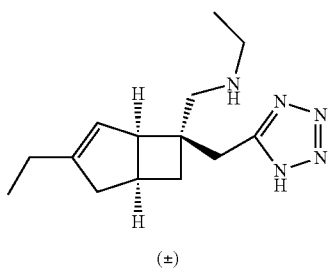 [SMILES: CCNC[C@]1(Cc2nnn[nH]2)C[C@H]2CC(CC)=C[C@H]21]

(±)

To a suspension of racemic ((1R,5S,6S)-6-((1H-tetrazol-5-yl)methyl)-3-ethylbicyclo[3.2.0]hept-3-en-6-yl)methanamine (compound of Formula 2) (50 mg, 0.214 mmol) in dry dichloroethane (10 ml) was added acetaldehyde (121 Ξl, 2.143 mmol) and the mixture stirred for 20 mins during which time the solution went clear.

The solvent was removed via rotary evaporation and the residue taken up into ethanol (10 ml) and to this solution was added sodium borohydride (81 mg, 2.143 mmol) and the mixture stirred for 20 mins.

The reaction mixture was acidified to pH 1 by the dropwise addition of 1N hydrochloric acid and the resultant mixture evaporated to dryness.

The crude product was purified by preparative HPLC (Waters, Basic (0.1% Ammonium Bicarbonate), Basic, Waters X-Bridge Prep-C18, 5 µm, 19×50 mm column, 20-50% acetonitrile in Water) to afford N-(((1R,5S,6S)-6-((1H-tetrazol-5-yl)methyl)-3-ethylbicyclo[3.2.0]hept-3-en-6-yl)methyl)ethanamine (24mg, 0.090 mmol, 42.0% yield) as a colourless solid.

LCMS (Agilent, Basic, Waters X-Bridge C18, 2.5 um, 4.6×30 mm, Basic (0.1% Ammonium Bicarbonate) 4 min method, 5-95% acetonitrile/water): m/z 262(M+H)$^+$ (ES$^+$); 260(M−H)$^−$ (ES$^−$), at 1.32 min, 98% purity@215 nm. $^1$H NMR (400 MHz, CD$_3$OD): δ 5.35 (1H, d, J=1.8), 3.25 (2H, dd, J=16.0, 13.0), 3.18-3.12 (3H, m), 3.08 (1H, d, J=15.5), 2.99 (1H, d, J=15.5), 2.88 (1H, quin, J=7.4), 2.52 (1H, dd, J,=16.4, 7.8), 2.21-2.16 (2H, m), 2.10 (1H, d, J=16.4), 1.99 (1H, ddd, J=12.4, 8.7, 2.7), 1.60 (1H, dd, J=12.4, 7.5), 1.40 (3H, t, J=7.3), 1.12 (3H, t, J=7.4) ppm.

$^{13}$C NMR (100 MHz, CD$_3$OD): δ 160.10, 151.80, 122.38, 56.59, 53.89, 45.05, 44.50, 42.99, 37.25, 31.93, 31.08, 25.39, 12.80, 11.53 ppm.

Example 4

Alternative Route for Preparation of Compound 10

Step 1 (Compound of Formula 14)

Racemic (2E/Z)-2-((1R,5S)-3-ethyl-6-bicyclo[3.2.0]hept-3-enylidene)acetonitrile

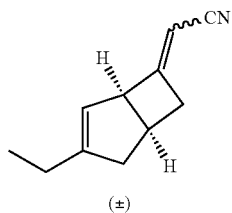

(±)

To a solution of 1.78M potassium tert-butoxide in tetrahydrofuran (64 mL, 113.9 mmol) diluted with tetrahydrofuran (45 mL) and cooled to 0° C. was added diethyl cyanomethylphosphate (21.16 g, 119 mmol). The reaction mixture was stirred at 0° C. for 10 minutes and allowed to warm to room temperature and stirred for a further 30 minutes. The mixture was transferred to a pressure equalising dropping funnel and added dropwise to a solution of racemic (1R,5S)-3-ethylbicyclo[3.2.0]hept-3-en-6-one (14.8 g, 109 mmol) in tetrahydrofuran (140 mL) at 0° C. The mixture was allowed to warm to room temperature and stirred for 18 hours.

The mixture was diluted with saturated aqueous ammonium chloride (100 mL) and ethyl acetate (200 mL) and the layers separated. The aqueous layer was extracted with ethyl acetate (50 mL) and the combined organic layers washed with brine (50 mL) and dried over magnesium sulfate. The residue after filtration was purified by chromatography on silica (2.5% ethyl acetate:isohexane) to afford racemic (2E)-2-((1R,5S)-3-ethyl-6-bicyclo[3.2.0]hept-3-enylidene)acetonitrile as a mixture of E/Z isomers (14.45 g, 84%).

LCMS (Agilent, Waters SunFire C18, 4.6×30 mm, Formic acid, acetonitrile water): m/z 160.2 (M+H)+ES+at 2.88 min.

1H NMR (400 MHz, CDCl3): ~60:40 mixture of alkene isomers δ 5.43 (0.4H, m), 5.23 (0.6H, m), 5.09 (0.6H, m), 4.98 (0.4H, m), 4.12 (0.4H, br s), 3.93 (0.6H, br s), 3.19-2.90 (2H, m), 2.74-2.46 (2H, m), 2.29-2.07 (2H, m), 1.14-1.06 (3H, m).

Step 2 (Compound of Formula 6)

Racemic 2-((1R,5S,6S)-3-ethyl-6-(nitromethyl)bicyclo[3.2.0]hept-3-en-6-yl)acetonitrile

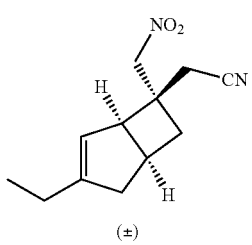 [SMILES: CCC1=C[C@@H]2[C@H](C1)C[C@@]2(CC#N)C[N+](=O)[O-]]

(±)

To a solution (1R,5S)-3-ethylbicyclo[3.2.0]hept-3-en-6-one (9.59 g, 60.3 mmol) in nitromethane (75 mL, 84.6 g, 1.38 mol) under nitrogen was added 1,8-diazabicyclo[5.4.0]undec-7-ene (10 mL, 10.2 g, 66 9 mmol) and the mixture stirred for 18 hours at room temperature.

The reaction mixture was poured into a 5% aqueous solution of potassium dihydrogen orthophosphate (400 mL) and ethyl acetate (300 mL) added. The layers were separated and the aqueous layer further extracted with ethyl acetate (2×150 mL). The combined organic layers were dried over magnesium sulfate and evaporated to afford a crude product which was combined with the crude product of a previous reaction performed on half the scale. The residue was purified by chromatography on silica (5-10% ethyl acetate:isohexane) to afford racemic 2-((1R,5S,6S)-3-ethyl-6-(nitromethyl)bicyclo[3.2.0]hept-3-en-6-yl)acetonitrile (16.5g, 75 mmol, 83% yield) as a ~2:1 mixture of diastereomers. Data for major diastereomer.

LCMS (Agilent, Waters SunFire C18, 4.6×30 mm, Acidic (0.05% formic acid, 6 min method, 3-97% acetonitrile/water): m/z 221 (M+H)+ (ES+) at 2.79 min.

1H NMR (400 MHz, DMSO-d6): δ 5.32 (1H, d, J=2.1), 4.87 (2H, s), 3.16 (1H, br. s), 2.97-2.82 (1H, m), 2.65 (2H, s), 2.48-2.40 (1H, m), 2.23 (1H, ddd, J=12.4, 8.8, 2.5), 2.16-2.02 (3H, m), 1.56 (1H, dd, J=12.5, 7.2), 1.07 (3H, t, J=7.5) ppm.

Step 3 (Compound of Formula 10)

Racemic 5-(((1R,5S,6S)-3-ethyl-6-(nitromethyl)-6-bicyclo[3.2.0]hept-3-enyl)methyl)-1H-tetrazole

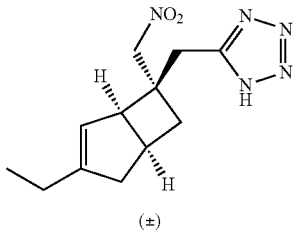 [SMILES: CCC1=C[C@@H]2[C@H](C1)C[C@@]2(Cc1nnn[nH]1)C[N+](=O)[O-]]

(±)

To a solution of racemic 2-((1R,5S,6S)-3-ethyl-6-(nitromethyl)bicyclo[3.2.0]hept-3-en-6-yl)acetonitrile (200 mg, 0.909 mmol) in dry toluene (4 mL) was added azidotrimethylsilane (590 μL, 4.44 mmol) and dibutyltin oxide (113 mg, 0.45 mmol). The vessel was sealed and heated to 110° C. for 18 hours. The mixture was cooled to room temperature and partitioned between water (20 mL) and ethyl acetate (20 mL). The organic layer was treated with 2M sodium hydroxide solution (20 mL) and the aqueous layer separated and then acidified with conc. hydrochloric acid to ~pH1. The acidic aqueous layer was re-extracted with ethyl acetate (2×20 mL) and the combined organic layers dried over magnesium sulfate. Filtration and evaporation gave a crude product with was purified by chromatography on silica (50% ether:isohexane) to afford racemic 5-(((1R,5S,6S)-3-ethyl-6-(nitromethyl)-6-bicyclo[3.2.0]hept-3-enyl)methyl)-1H-tetrazole (10 mg, 0.038 mmol, 4% yield).

LCMS (Agilent, Waters SunFire C18, 4.6×30 mm, Acidic (0.05% formic acid, 6 min method, 3-97% acetonitrile/water): m/z 264 (M+H)+ (ES+); 262 (M−H)− (ES−), at 2.35 min. 1H NMR (400 MHz, DMSO-d6): δ 11.09 (1H, br. s), 5.37 (1H, d, J=1.2), 4.80 (2H, s), 3.22 (1H, br. s), 3.01 (2H, s), 2.93 - 2.81 (1H, m), 2.50-2.40 (1H, m), 2.19-2.05 (4H, m), 1.63 (1H, dd, J=12.5, 7.5), 1.05 (3H, t, J=7.6) ppm.

Alternative Conditions for Step 3 (Compound of Formula 10)

Racemic 5 -(((1R,5S,6S)-3-ethyl-6-(nitromethyl)-6-bicyclo[3.2.0]hept-3 -enyl)methyl)-1H-tetrazole To a solution of racemic 2-((1R,5S,6S)-3-ethyl-6-(nitromethyl)bicyclo[3.2.0]hept-3-en-6-yl)acetonitrile (170 mg, 0.772 mmol) in 1-methyl-2-pyrrolidinone (2.7 mL) was added pyridine hydrochloride (180 mg, 1.57 mmol) and sodium azide (263 mg, 4.04 mmol). The flask was heated under nitrogen to 100° C. for 18 hours. The flask temperature was then increased to 117-120° C. for a further 4 hours after which it was allowed to cool to room temperature. The mixture was poured into water (20 mL) and carefully acidified with aqueous 2M hydrochloric acid. The aqueous layer was extracted with ethyl acetate (2×20 mL) and then the organic layer shaken with a 2M sodium hydroxide solution (1×20 mL, 1×10 mL). The combined aqueous layers were then acidified with conc. hydrochloric acid to ~pH1 and re-extracted with ethyl acetate (3×20 mL). The combined organic layers were washed with water (10 mL) and dried over magnesium sulfate. Filtration and evaporation gave a crude product with was purified by chromatography on silica (7 g silica, diethyl ether:isohexane:acetic acid 200:300:8) to afford racemic 5-(((1R,5S,6S)-3-ethyl-6-(nitromethyl)-6-bicyclo[3.2.0]hept-3-enyl)methyl)-1H-tetrazole (81 mg, 0.304 mmol, 40% yield).

LCMS (Agilent, Waters SunFire C18, 4.6×30 mm, Acidic (0.05% formic acid, 6 min method, 3-97% acetonitrile/water): m/z 264 (M+H)$^+$(ES$^+$); 262 (M−H)$^-$(ES$^-$), at 2.35 min 1H NMR (400 MHz, DMSO-d6): δ 16.10 (1H, br. s), 5.34 (1H, d, J=1.4), 4.80 (2H, s), 3.22 (1H, br. s), 3.02 (2H, s), 2.94-2.81 (1H, m), 2.48-2.40 (1H, m), 2.19-2.05 (4H, m), 1.64 (1H, dd, J=12.5, 7.4), 1.05 (3H, t, J=7.4) ppm.

Example 5

The therapeutic activity of the compounds of the present invention has been demonstrated by an $\alpha_2\delta$-1 binding affinity assay. This test was carried out in the following way.

Calcium Channel $\alpha_2\delta$-1 Subunit Binding Assay

This section describes a scintillation proximity assay (SPA) to measure [$^3$H] gabapentin ([$^3$]GBP) binding to membranes containing $\alpha_2\delta$-1 and its use for profiling compounds (Calvo et al (2012) J. Biomol. Screen. 17:1041-1049).

Human Cav1.2/β3/$\alpha_2\delta$-1 Calcium Channel Membranes (Chantest) were thawed on ice, aliquotted and stored at −80° C. for subsequent use. Membranes were diluted to 200 μg/ml (3 μg/well final assay concentration (FAC)) in assay buffer (10 mM HEPES (Sigma), (pH7.4)). The [$^3$H]GBP (Perkin Elmer) stock solution was stored at −20° C. [$^3$H]GBP was diluted to 40 nM (10 nM FAC) in assay buffer. SPA beads (Perkin Elmer) were re-suspended at 100 mg/ml in 10 mM HEPES (pH 7.4). Beads were diluted to 40 mg/ml (0.6 mg/well FAC) in assay buffer. Nonspecific binding (NSB) was generated using an excess of pregabalin (Tocris). Pregabalin was solubilized in Milli-Q H$_2$O at 10 mM. 10 mM pregabalin was diluted to 400 μM (100 μM FAC) in assay buffer.

Compounds were diluted to 100 μM then half log diluted. These were then diluted 1:100 in assay buffer to a 4× assay concentration (1 μM FAC top dilution).

SPA beads 15 μl; membranes 15 μl; pregabalin or assay buffer/test compound 15 μl and [$^3$H]GBP 15 μl were added to a white 96 well isoplate, (Perkin Elmer). The assay plate was sealed and mixed for 10s on a plate shaker then placed into a plate rack and slotted into the reader stacker. The plate was incubated overnight (20 hours) then read on a 1450 MicroBeta TriLux Microplate Scintillation and Luminescence Counter at ambient room temperature (RT).

Data Analysis

The NSB values obtained by adding 100 μM pregabalin were subtracted from values obtained for compounds to generate a specific binding value. Specific binding in counts per minute (cpm) were plotted against compound concentration (M) and fitted using a 4 parameter logistic equation. Compound IC$_{50}$ values were calculated, where the concentration of compound produces a 50% inhibition of specific binding. The results of test compounds are shown in Table 1.

TABLE 1

Synthesised compounds and $\alpha_2\delta$-1 binding affinity data: IC$_{50}$ values for compounds tested in the [$^3$H] gabapentin binding assay using cell membranes expressing recombinant $\alpha_2\delta$-1 with the $\beta_3$ ancillary protein (Chan test)

| NVA (ID) | Structure | IC$_{50}$ (nM) Overnight Incubation (Geometric mean) | Literature IC$_{50}$ nM |
|---|---|---|---|
| Pregabalin | ![structure] | 23 (n = 12) | 80 |
| Formula 2 (Racemic) | ![structure] | 4.2 (n = 10) | † |

TABLE 1-continued

Synthesised compounds and α₂δ-1 binding affinity data: IC₅₀ values for
compounds tested in the [³H] gabapentin binding assay using cell membranes expressing
recombinant α₂δ-1 with the β₃ ancillary protein (Chan test)

| NVA (ID) | Structure | IC₅₀ (nM) Overnight Incubation (Geometric mean) | Literature IC₅₀ nM |
|---|---|---|---|
| Formula 3 (Racemic) | (structure) | 19 (n = 2) | † |
| Formula 2 peak 1 (Chiral) | (structure) Peak 1 | 165 (n = 3) | † |
| Formula 2 peak 2 (chiral) | (structure) Peak 2 | 2.1 (n = 6) | † |
| Formula 1 (Racemic) | (structure) | ≥500 (n = 2) | † |

†: No relevant literature.

Example 6

Method for determining kinetic binding parameters (association and dissociation rates) and affinities (KD) of GABA analogues to $α_2δ$-1subunits.

It is well known in the art that binding affinity can be expressed as KD or equilibrium dissociation constant, whereby increasing binding affinity correlates with decreasing KD, which can be calculated from kinetic binding constants. Kinetic binding analysis of GABA analogues to $α_2δ$-1subunits can be determined by surface plasmon resonance technology applied in Biacore™ SPR instruments (Biacore, GE Healthcare, Uppsala). Kinetic association rates (ka; k-on) and dissociation rates (kd; k-off) are obtained. Equilibrium dissociation constant (KD; affinity) values are calculated as k-off/k-on.

In the prior art and in scientific publications a short region within the full length Voltage-Gated Calcium Channel subunit $α_2δ$-1 is referred to as the binding site for gabapentin and pregabalin (Wang et al (1999) Biochem. J. 342, 313-320; Field et al (2006) Proc. Natl. Acad. Sci. U.S.A, 14, 103, 17537-17542).

This example discloses that the GABA analogues ((1R, 5S,6S)-6-((1H-tetrazol-5-yl)methyl)-3-ethylbicyclo[3.2.0]hept-3-en-6-yl)methanamine ("Test Compound": prepared as described in Example 2) and (1R,5S,6S)-6-(aminomethyl)-3-ethylbicyclo[3.2.0]hept-3-en-6-yl]acetic acid ("Reference Compound": prepared as described in WO 2010/079668 and US 2012/0071685A1) are capable of binding to a recombinant fragment of human Voltage-Gated Calcium Channel subunit ($α_2δ$-1, CACNA2D1). Furthermore, comparative kinetic binding analysis of these two compounds was performed in order to identify and characterise potentially different binding properties of these two compounds for their target (CACNA2D1).

Human recombinant CACNA2D1 was covalently immobilized at high density (26000 RU) to the surface of a Biacore CM5 optical sensor chip as target ligand using thiol coupling chemistry, according to manufacturer's instructions (Biacore Thiol Coupling Kit,Order Code: BR-10057; GE-Healthcare, Uppsala). Bovine serum albumin was immobilised on a reference flow cell in order to compensate for non-specific background binding. Increasing concentrations of the Test Compound and the Reference Compound, dissolved in Biacore HBS-P buffer (Order Code: BR-100368; GE-Healthcare, Uppsala), were passed across the flow cells at a flow rate of 30 µl/min The sensor chip surfaces were regenerated after each run with 10 mM hydrochloric acid (flow rate=30 µl/min.) in order to remove pre-bound material and reconstitute active compound binding sites. Subtractive sensorgrams (CACNA2D1 recombinant protein minus BSA reference) were then generated.

Kinetic binding analysis was subsequently carried out by mathematical single sensorgram fitting of each subtractive binding sensorgram using a Langmuir 1:1 interaction algorithm as provided by BiaEvaluation 4.0 software.

The experimental results described in the current example revealed that both compounds under investigation were able to specifically bind to human CACNA2D1 recombinant protein. Furthermore, the data disclosed in this example allow to differentiate the binding properties between the Test Compound and the Reference Compound. These differences are predictive of increased pharmacological activity of the Test Compound over the Reference Compound.

It will be understood that the above examples are intended as illustrations of the present invention and are not intended to be limiting in any way. The scope of the invention should, therefore, be determined with reference to any appended claims, along with the full scope of equivalents to which such claims are entitled.

The invention claimed is:

1. A method of administering to a human subject a pharmaceutical composition, the pharmaceutical composition comprising a pharmaceutically acceptable carrier and a compound of Formula 1

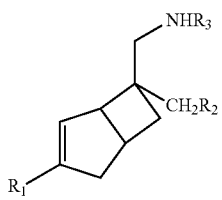

Formula 1 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_{2-4}$ alkynyl group or a $C_{3-7}$ cycloalkyl group;

$R_2$ represents

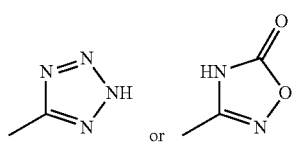

or a tautomer thereof; and $R_3$ represents hydrogen, a $C_{1-4}$ alkyl group, a ($C_{1-4}$ alkoxy)($C_{2-4}$ alkyl) group or a $C_{3-7}$ cycloalkyl group; or a pharmaceutically acceptable salt or solvate thereof; wherein the method comprises: (i) providing the human subject with the pharmaceutical composition, wherein the pharmaceutical composition is in a form for administration to a human subject, the form selected from the group consisting of a capsule, a caplet, a tablet, and a topical ointment; (ii) administering the form to the human subject, wherein the administering is selected from the group consisting of orally, rectally, parenterally, and topically; and (iii) allowing the compound to bind to an $α_2δ$-1subunit of a voltage-gated calcium channel, wherein the voltage-gated calcium channel is embedded within a cell plasma membrane of the human subject.

2. The method according to claim 1, the compound having the Formula 2

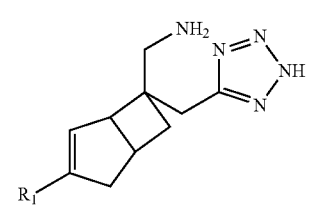

Formula 2 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_{2-4}$ alkynyl group or a $C_{3-7}$ cycloalkyl group;

or a pharmaceutically acceptable salt or solvate thereof.

3. The method according to claim 1, the compound having the Formula 3

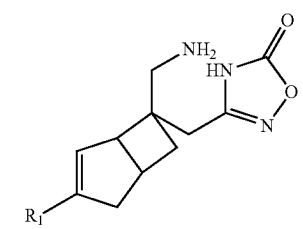

Formula 3 wherein $R_1$ represents hydrogen, halo, a $C_{1-4}$ alkyl group, a $C_{1-4}$ alkylhalide group, a ($C_{1-4}$ alkoxy)($C_{2-4}$ alkyl) group, a $C_{2-4}$ alkenyl group, a $C_{2-4}$ alkynyl group or a $C_{3-7}$ cycloalkyl group;

or a pharmaceutically acceptable salt or solvate thereof.

4. The method according to claim 1, the compound in which $R_1$ represents ethyl.

5. The method according to claim 1, the compound having the Formula 4

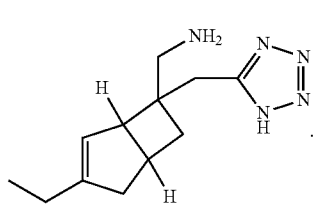

Formula 4

6. The method according to claim 5, the compound having the Formula 4a

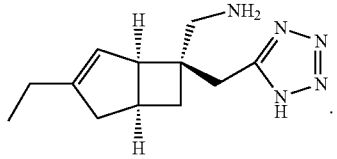

Formula 4a

7. The method according to claim 3, the compound having the Formula 5

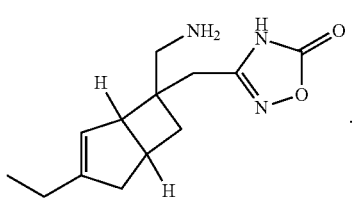

Formula 5

8. The method according to claim 1, wherein the human subject has neuropathic pain.

9. The method according to claim 1, wherein the human subject has a disorder of the central nervous system.

10. The method according to claim 1, wherein the human subject has a disease of the central nervous system and/or the peripheral nervous system.

11. The method according to claim 1, wherein the human subject has a headache and/or a migraine.

12. A method of treating neuropathic pain in a patient in need thereof comprising administering a therapeutically effective amount of a compound of Formula 1 or a pharmaceutically acceptable salt or solvate thereof as defined in claim 1.

13. A method of treating disorders of the central nervous system in a patient in need thereof comprising administering a therapeutically effective amount of a compound of Formula 1 or a pharmaceutically acceptable salt or solvate thereof as defined in claim 1.

14. A compound of Formula 1 as defined in claim 1 for use in the treatment of neuropathic pain.

15. A compound of Formula 1 as defined in claim 1 for use in the treatment of diseases of the central and/or the peripheral nervous system.

16. A compound for the use according to claim 15 for use in the treatment of diseases of the central nervous system.

17. A compound of Formula 1 as defined in claim 16 for use in the treatment headache and migraine.

* * * * *

UNITED STATES PATENT AND TRADEMARK OFFICE
CERTIFICATE OF CORRECTION

PATENT NO. : 9,750,720 B2
APPLICATION NO. : 15/359120
DATED : September 5, 2017
INVENTOR(S) : Premji Meghani and Franz Kricek It is certified that error appears in the above-identified patent and that said Letters Patent is hereby corrected as shown below:

On the Title Page

Item (74), Attorney, Agent or Firm is shown as:
Karer, Matthew Bell, Adam
Please correct this to:
Kaser, Matthew Bell, Adam Signed and Sealed this
Twelfth Day of June, 2018

Andrei Iancu
*Director of the United States Patent and Trademark Office*